(12) United States Patent
Gomes et al.

(10) Patent No.: US 11,517,727 B2
(45) Date of Patent: Dec. 6, 2022

(54) PERFUSION BALLOON WITH EXTERNAL VALVE

(71) Applicant: C.R. Bard, Inc., Tempe, AZ (US)

(72) Inventors: Garrett Gomes, San Mateo, CA (US); Anant Hegde, Hayward, CA (US); Jonathan Kurniawan, Belmont, CA (US); Andrew Moll, Burlingame, CA (US); Cameron Moore, Fremont, CA (US); Samuel Radochonski, San Francisco, CA (US)

(73) Assignee: C.R. BARD, INC., Franklin Lakes, NJ (US)

( * ) Notice: Subject to any disclaimer, the term of this patent is extended or adjusted under 35 U.S.C. 154(b) by 274 days.

(21) Appl. No.: 16/817,016

(22) Filed: Mar. 12, 2020

(65) Prior Publication Data
US 2020/0206484 A1 Jul. 2, 2020

Related U.S. Application Data

(62) Division of application No. 15/061,802, filed on Mar. 4, 2016, now Pat. No. 10,625,058.

(51) Int. Cl.
*A61M 25/10* (2013.01)
*A61M 29/02* (2006.01)

(52) U.S. Cl.
CPC .. *A61M 25/10185* (2013.11); *A61M 25/1002* (2013.01); *A61M 25/104* (2013.01); *A61M 29/02* (2013.01); *A61M 2025/1081* (2013.01); *A61M 2025/1097* (2013.01); *A61M 2210/125* (2013.01)

(58) Field of Classification Search
CPC .......... A61M 25/1018; A61M 25/1002; A61M 25/104; A61M 29/02; A61M 2025/1081; A61M 2025/1097; A61M 2210/125
See application file for complete search history.

(56) References Cited

U.S. PATENT DOCUMENTS

| 7,244,242 | B2 | 7/2007 | Freyman | |
|---|---|---|---|---|
| 2005/0090846 | A1 | 4/2005 | Pederson | |
| 2005/0288632 | A1* | 12/2005 | Willard | A61M 25/104 604/113 |

(Continued)

FOREIGN PATENT DOCUMENTS

| JP | 2008504067 A | 2/2008 |
|---|---|---|
| JP | 2014509218 A | 4/2014 |

(Continued)

*Primary Examiner* — Alexander J Orkin
(74) *Attorney, Agent, or Firm* — Dickinson Wright PLLC; Andrew D. Dorisio (57) ABSTRACT

An apparatus for performing a medical procedure and, in particular, an aortic valvuloplasty, in a vessel for transmitting a flow of fluid. The apparatus includes an inflatable perfusion balloon including an internal passage for permitting the fluid flow in the vessel while the perfusion balloon is in an inflated condition, the balloon including a plurality of cells in a single cross section and a covering for at least partially covering the cells. A valve associated with the balloon controls the fluid flow within the passage, the valve being arranged external to the passage. The valve may form a tubular extension of the covering, or may be separate from the covering, and may comprise flaps. A spiral covering may also form the valve.

9 Claims, 10 Drawing Sheets

(56) References Cited

U.S. PATENT DOCUMENTS

| | | | | |
|---|---|---|---|---|
| 2008/0039786 A1* | 2/2008 | Epstein | ............... | A61M 29/02 |
| | | | | 604/103.03 |
| 2009/0118681 A1 | 5/2009 | Molgaard-Nielsen | | |
| 2009/0228093 A1 | 9/2009 | Taylor et al. | | |
| 2012/0109179 A1* | 5/2012 | Murphy | ............. | A61M 25/104 |
| | | | | 606/200 |
| 2013/0226287 A1* | 8/2013 | Weber | ................... | A61B 17/22 |
| | | | | 623/2.1 |
| 2014/0066896 A1* | 3/2014 | Tilson | .................. | A61F 2/2433 |
| | | | | 604/509 |
| 2014/0350523 A1* | 11/2014 | Dehdashtian | ....... | A61M 1/3666 |
| | | | | 604/509 |

FOREIGN PATENT DOCUMENTS

| | | |
|---|---|---|
| WO | 89011307 A1 | 11/1989 |
| WO | 2006002268 A2 | 1/2006 |
| WO | 2012099979 A1 | 7/2012 |

\* cited by examiner

PERFUSION BALLOON WITH EXTERNAL VALVE

INCORPORATION BY REFERENCE

All publications and patent applications mentioned in this specification are herein incorporated by reference to the same extent as if each individual publication or patent application was specifically and individually indicated to be incorporated by reference.

The disclosure of U.S. patent application Ser. No. 15/061,802 filed Mar. 4, 2016 is incorporated by reference.

BACKGROUND

Expandable devices, such as balloons, are widely used in medical procedures. In the case of a balloon, it is inserted into a body, typically on the end of a catheter, until the balloon reaches the area of interest. Adding pressure to the balloon causes the balloon to inflate. In one variation of use, the balloon creates a space inside the body when inflated.

Balloons may be used in the valves associated with the heart, including during Balloon Aortic Valvuloplasty (BAV) (as described in Hara et al. "Percutaneous balloon aortic valvuloplasty revisited: time for a renaissance?" *Circulation* 2007; 115:e334-8) and Transcatheter Aortic Valve Implantation (TAVI)). For such a procedure, the inflated balloon may be designed to allow for continued blood flow, or perfusion. However, when the balloon is inflated, the heart valve is necessarily temporarily disabled. This can lead to disruptions in the blood flow, including by creating undesirable back flow.

Thus, it would be desirable to provide a perfusion balloon that can be used to regulate the flow of fluid during a procedure, especially when used in connection with a procedure involving a valve that is disabled as a result of the procedure or otherwise.

SUMMARY OF THE DISCLOSURE

The technical effect of the disclosed embodiments may be considered to include achieving valving external to a perfusion balloon, which creates an enhanced flow of fluid during the valve, enhanced blocking of the flow during the closing of the valve, and/or creates an easier manner to manufacture the balloon (especially in the case where it includes a non-compliant shell over the balloon). In one embodiment, a single valve may be used to regulate the flow through the entire passage allowing perfusion, such as by simultaneously blocking and unblocking multiple entrances to the passage.

According to one aspect of the disclosure, an apparatus for performing a medical procedure in a vessel for transmitting a flow of fluid. The apparatus comprises an inflatable perfusion balloon including an internal passage having a plurality of entrances for permitting the fluid flow in the vessel while the perfusion balloon is in an inflated condition. A valve is associated with the balloon for controlling the fluid flow within the passage. The valve is for selectively covering the entrances to the passage to control the flow of fluid therein. The valve thus includes a first condition or position spaced from the entrances for allowing fluid to flow into the internal passage and a second condition or position closer to the entrances than in the first condition or position for restricting the flow of fluid to the passage.

In one embodiment, the valve comprises a tube. The tube may have a generally circular, continuous cross-section. The balloon may comprise a generally tapered portion, and the tube extends along the generally tapered portion. The balloon may comprise a plurality of cells in a single cross-section, and a covering for covering the cells. The tube may be an extension of the covering. Each cell includes a neck in communication with an inflation lumen of a shaft supporting the balloon, and tube may overlie the necks. The tube may be located at a proximal end portion of the balloon.

According to a further aspect of the disclosure, an apparatus for performing a medical procedure in a vessel for transmitting a flow of fluid is provided. The apparatus comprises an inflatable perfusion balloon including an internal passage for permitting the fluid flow in the vessel while the perfusion balloon is in an inflated condition. A valve associated with the balloon is provided for controlling the fluid flow within the passage. The valve comprises a plurality of elongated flaps for covering the entrance.

In one embodiment, the flaps are fixed at a proximal end (that is, at the end corresponding to the shaft supporting the balloon) for selectively covering an entrance to the passage to control the flow of fluid therein. The fixed proximal end is connected to the balloon, and the flaps each include a distal end that is not connected to the balloon. The balloon may comprise a generally tapered portion, and the flaps may extend along the generally tapered portion. The flaps may each include a distal end connected to the balloon by a tether. The flaps may be narrower at the fixed proximal end that at a distal end. A sheath may also be provided for covering any valve disclosed herein, such as for example the extension of the tube, the plurality of flaps or otherwise.

Still a further aspect of the disclosure pertains to an apparatus for performing a medical procedure in a vessel for transmitting a flow of fluid. The apparatus comprises an inflatable perfusion balloon including an internal passage for permitting the fluid flow in the vessel while the perfusion balloon is in an inflated condition. A valve is associated with the balloon for controlling the fluid flow within the passage, the valve comprising a spiral covering adapted for compressing to restrict fluid flow to or from the passage and for expanding to permit fluid flow to or from the passage.

In one embodiment, the spiral covering comprises an elongated piece of material wound spirally over the balloon. The spiral covering comprises a material having a frusto-conical with a spiral cut therein. The balloon may comprise a generally tapered portion, and the spiral covering extends along the generally tapered portion.

The balloon may comprise a plurality of cells in a single cross-section, and a covering for covering the cells, and wherein the spiral covering is an extension of the covering. Each cell may have a neck in communication with an inflation lumen of a shaft supporting the balloon, and wherein the spiral covering overlies the necks. The spiral covering may be located at a proximal end portion of the balloon.

Yet another aspect of the disclosure pertains to an apparatus for performing a medical procedure in a vessel for transmitting a flow of fluid. The apparatus comprises an inflatable perfusion balloon including an internal passage for permitting the fluid flow in the vessel while the perfusion balloon is in an inflated condition. The balloon includes a plurality of cells in a single cross section and a covering for at least partially covering the cells. A valve associated with the balloon is for controlling the fluid flow within the passage, the valve being arranged external to the passage and separate from the covering, which may be non-compliant.

In one embodiment, the valve comprises a material having a generally frusto-conical shape and extending along a tapered portion of the balloon, the material including a plurality of openings (such as for example, slits) for allowing fluid flow to or from the passage, which may be covered by flaps. The valve may comprise a spiral covering extending along a tapered portion of the balloon. The valve may comprise a plurality of elongated flaps for selectively covering an entrance to the passage to control the flow of fluid therein, the flaps having a fixed proximal end. As noted above, any embodiment may include a sheath for at least partially covering the valve.

DETAILED DESCRIPTION

The invention disclosed pertains to an inflatable device in the nature of a perfusion balloon. The novel features of the invention are set forth with particularity in the claims that follow. A better understanding of the features and advantages of the invention will be obtained by reference to the following detailed description that sets forth illustrative embodiments, in which the principles of the invention are utilized, and the accompanying drawings.

Figure 1:
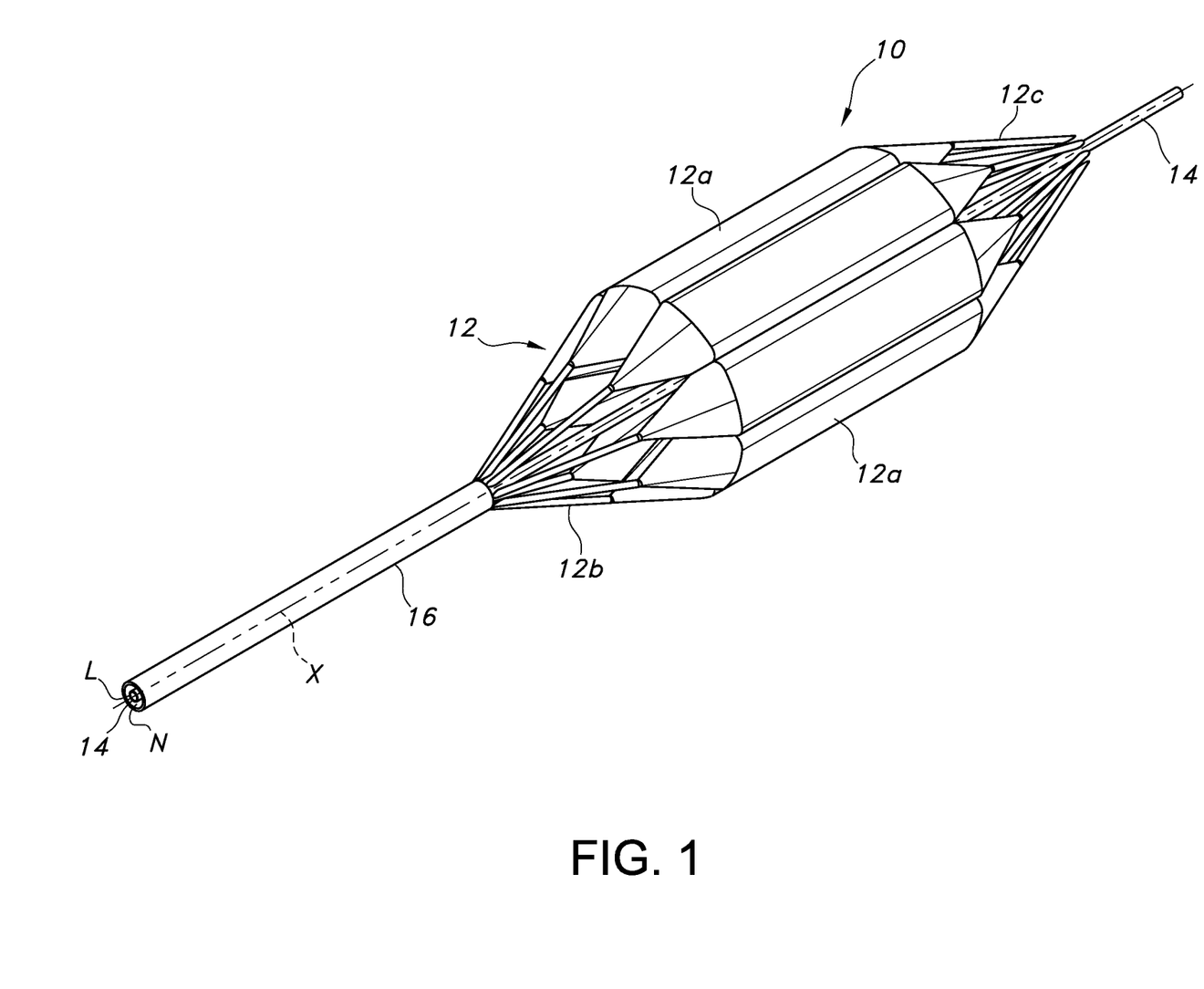
FIG. 1 is a perspective view of an inflatable device in the expanded condition.
Figure 2:
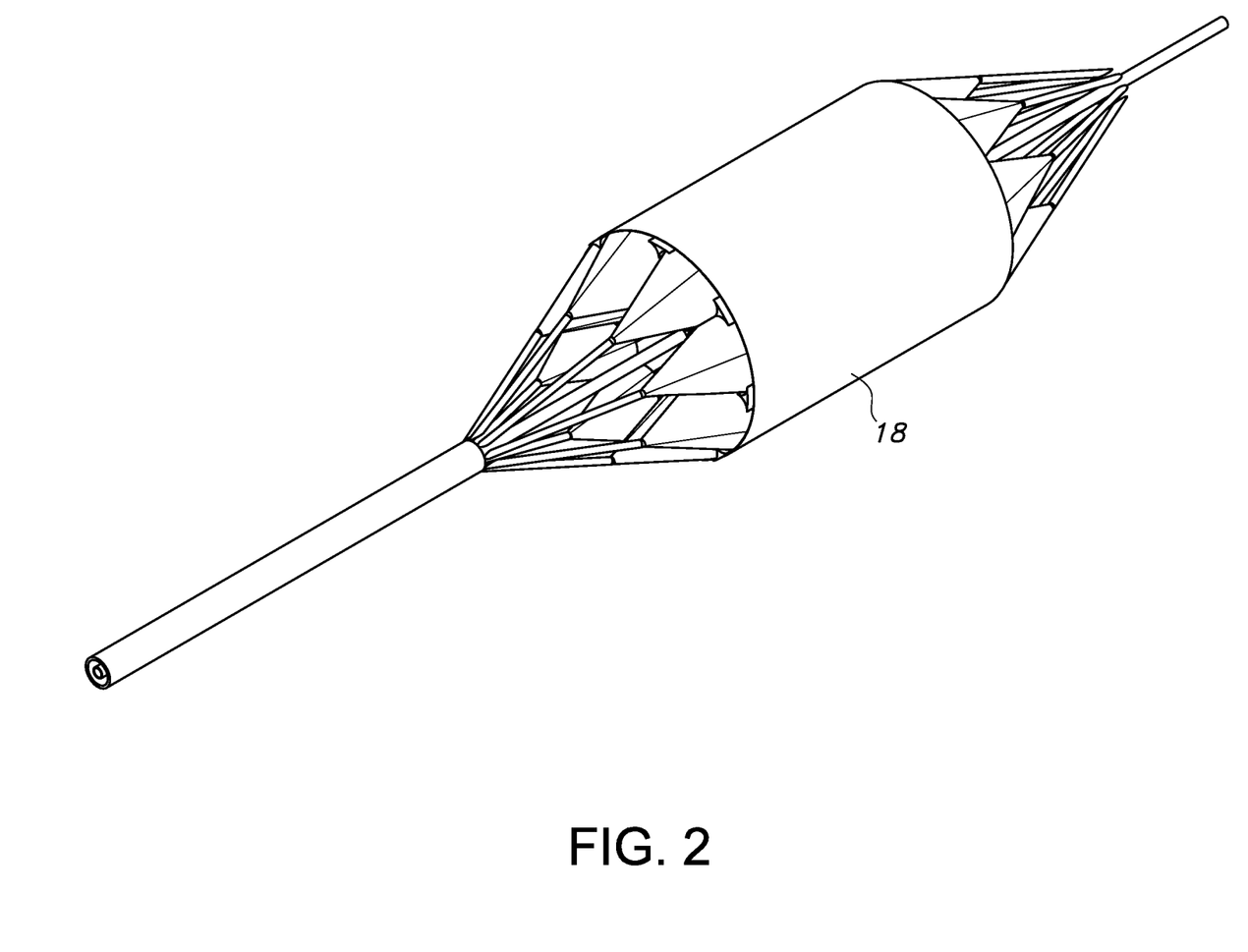
FIG. 2 is a perspective view of an inflatable device in the expanded condition, and including an outer covering or shell.

FIG. 1 shows an inflatable device 10 including a perfusion balloon 12 in an inflated condition, ready for use in connection with a procedure (but which balloon would normally be folded for purposes of delivery through the vasculature to a selected treatment area, such as the aortic valve). From viewing the inflated condition, it can be understood that the balloon 12 of the device 10 may have multiple inflatable cells 12a (eight shown, but any number may be provided) in at least a single cross-section of the balloon. As indicated in FIG. 2, a retainer, such as a tubular, flexible sheath or covering 18 forming a shell or jacket may be provided over the central portion of the cells 12a to retain them in a generally annular configuration in the illustrated embodiment, and may also serve to protect the cells when contact is made with a stenosed valve or the like. The covering 18 may be non-compliant to prevent further expansion once the cells 12a are fully inflated.

The cells 12a may be individual or discrete, separately inflatable balloons. Each cell 12a having a separate inflation lumen via neck 12b, as noted, and also a neck 12c at the distal end, which form generally tapered portions of the balloon 12. The cells 12a may be sealed at a distal tip (such as at the distal end of each neck 12c), or may be parts of a single balloon. The latter may be achieved by a segmented, elongated structure folded in a manner that causes the cells 12a to form a passage P extending along a central axis X, along which fluid such as blood may continue to flow, even when the balloon 12 is fully inflated (which may be done through a single inflation lumen, or each balloon could have its own inflation lumen). A full description of this type of balloon may be found in International Patent Application Publication No. WO2012099979A1. However, other forms of perfusion balloons could also be used, such as for example a tubular balloon, one having a peripheral (e.g., helical) channel for purposes of allowing fluid flow to occur during inflation, or any combination of these technologies.

In any case, the device 10 may also include an inner shaft or tube 14 including a lumen L extending along the central axis X, which may be adapted for receiving a guidewire for guiding the device to a treatment location. The inner tube 14 may form part of a catheter shaft or tube 16, which includes a lumen N in which the inner tube 14 is positioned. The perfusion balloon 12 may in turn be attached to and supported by the catheter shaft 16, such as at or adjacent the proximal necks 12b forming the entrance to passage P, which may receive inflation fluid through the lumen N.

According to one aspect of the disclosure, the balloon 12 is adapted for selectively regulating the flow of fluid through the passage P. In one disclosed embodiment, this is achieved using a valve 20 external to the balloon 12 (that is, not located within passage P or the interior space between the necks 12b, 12c and the shaft or tube 14) that selectively actuates in a passive manner, such as an extension 18a of the covering 18. The extension 18a is arranged for allowing flow through the passage P in a first position or condition when unactuated (FIGS. 3 and 4), for example such that the single extension blocks the multiple entrances to the passage. In a second position or condition, the valve 20 formed by extension 18a may cover the entrance to the passage P (that is, the spaces between the necks 12b of cells 12a) to substantially block it (note extension 18a' in FIG. 5) and thus retard or prevent fluid flow when actuated (which may be achieved passively as the result of the flow of fluid in the corresponding vessel resulting from circulation). The valve may thus repeatedly and regularly restrict and allow fluid flow through the passage P when the balloon 12 is inflated, such as in the space including the aortic valve, and thus mimics the function of the otherwise disabled valve. Consequently, the extension 18 (which may be a single element in this embodiment, despite covering one or more entrances to the passage P) provides a one way valve function during a procedure using the device 10.

Figure 3:
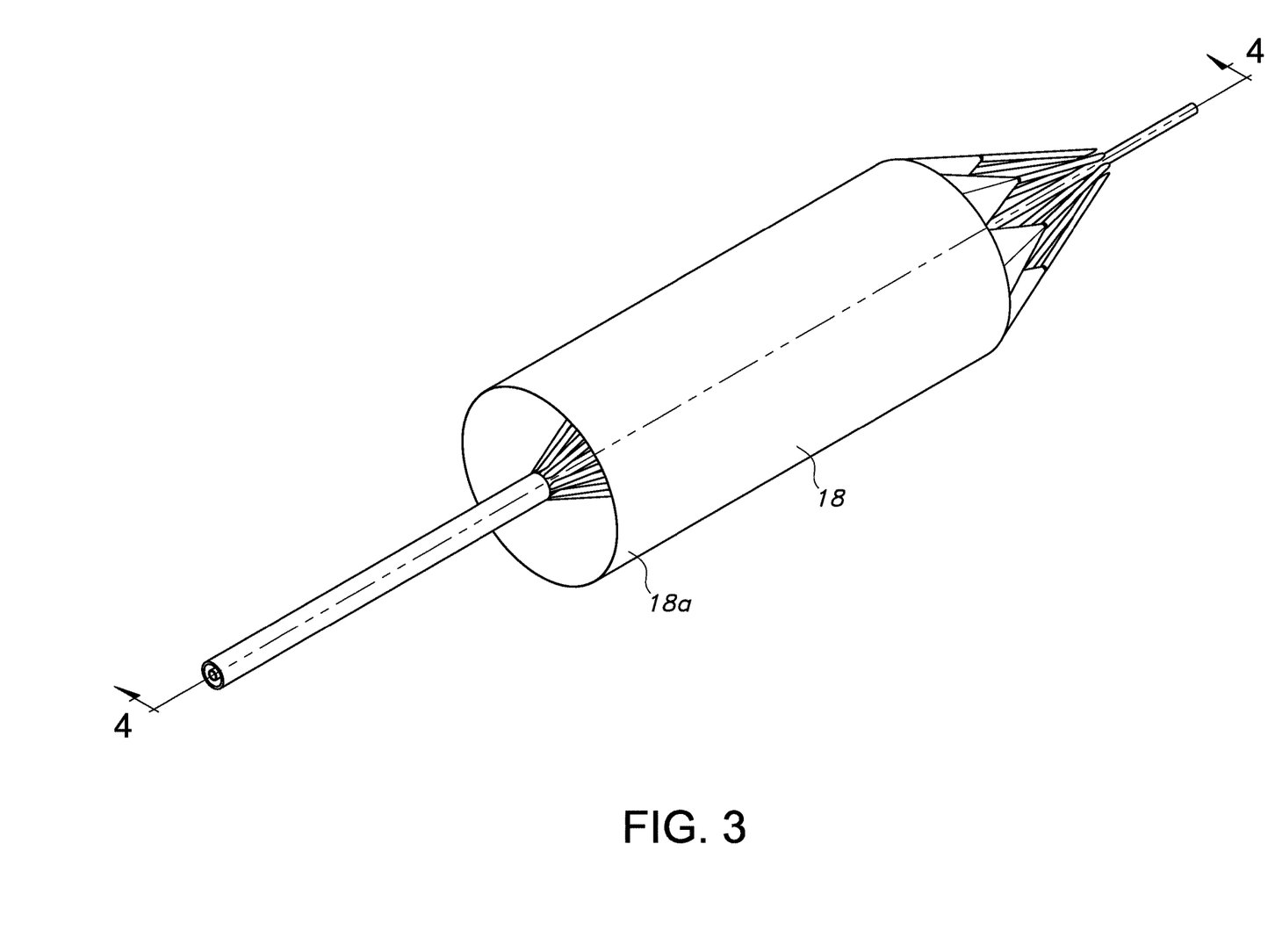
FIG. 3 is a perspective view of an inflatable device including an extended covering or shell forming a valve.
Figure 4:
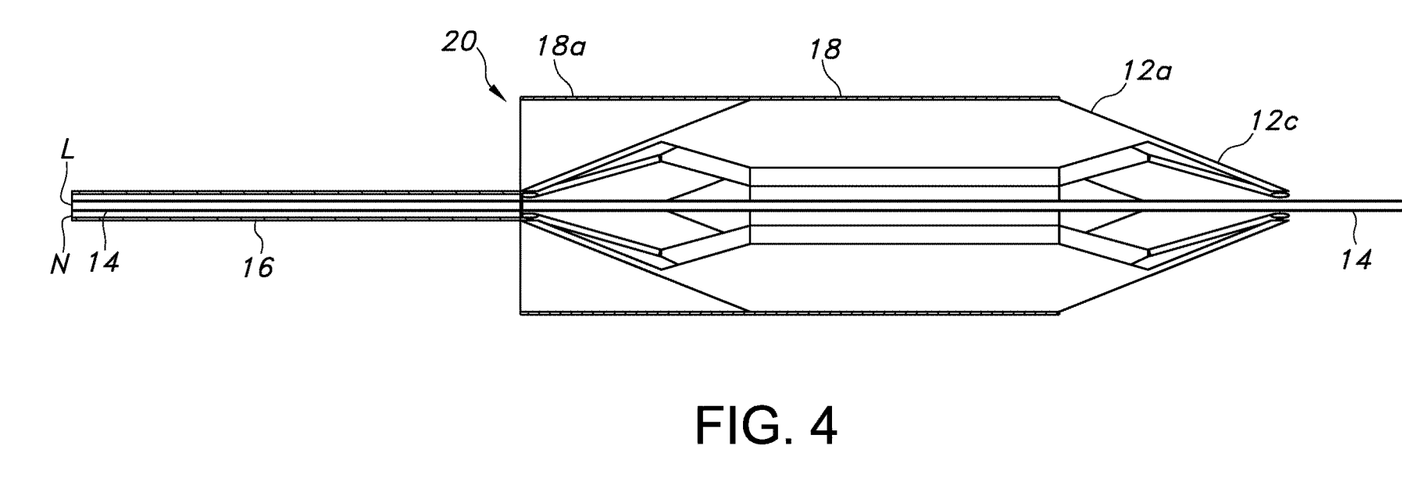
FIG. 4 is a cross-sectional view along line 4-4 of FIG. 3 with the valve in a first position for permitting flow through a central passage of the device.
Figure 5:
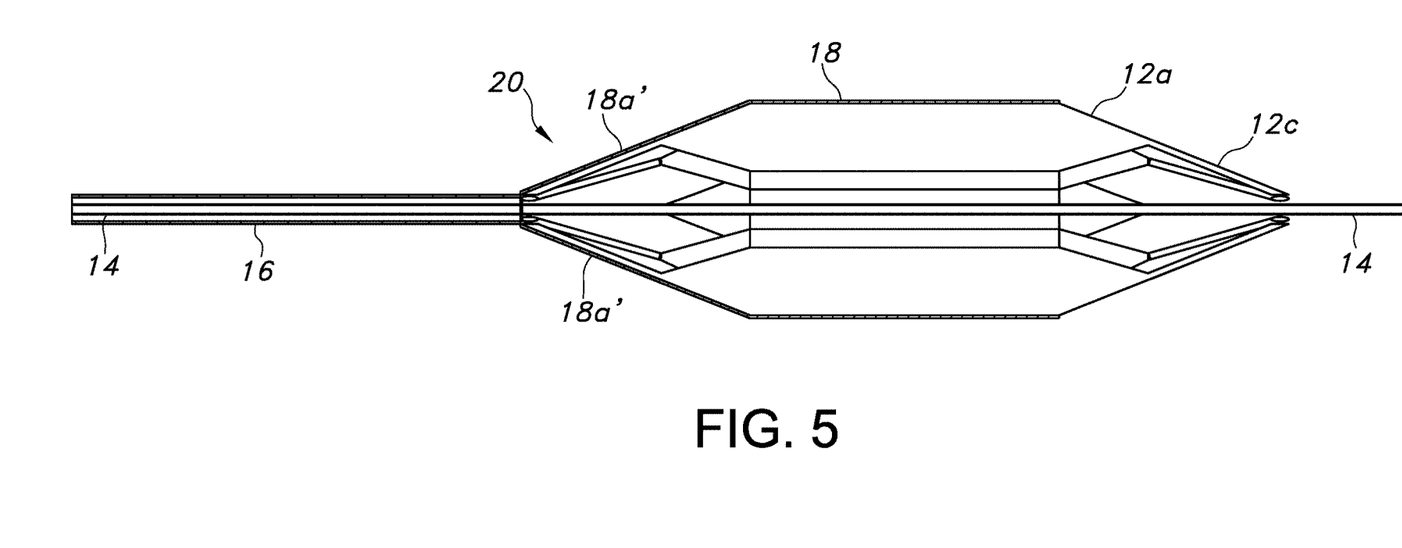
FIG. 5 is a cross-sectional side view of the device of FIG. 4, with the valve in a second position for restricting flow through a central passage of the device.

The extension 18*a* may be formed of a flexible material having a generally tubular shape, and may have a generally circular cross-section. The material forming the extension 18*a* may be continuous, but could also be provided in two or more segments in order to achieve the valving function (e.g., two segments to simulate a bicuspid valve, three to simulate a tricuspid, etc.). The extension 18*a* may also form a unitary structure with the covering 18, but could also be a separate structure attached to the balloon 12 (either in juxtaposition with the covering, or as a layer above or below it). The length of the extension 18*a* may be selected to provide the appropriate covering for the entrance to the passage P when folded, which of course will depend on the size and geometry of the balloon 12.

The material forming the valve 18 may also optionally be provided with properties to facilitate preferential folding when the balloon 12 is collapsed, and then expanded. This may be achieved, for example, by the use of different thickness of material to create a living hinge or like structure that causes the material to fold in a certain manner. The material of the valve body may also be provided with fold lines, pleats, or supports to cause folding and unfolding to occur in a preferential manner to ensure that the valve 18 expands or collapses in the intended way to achieve the desired valving function.

As noted, the external valve 20 may also be provided as a structure separate from the jacket or covering 18 over the central portion of balloon 12. As one example, reference is made to FIGS. 6-8, which illustrate an embodiment in which the valve 20 comprises a plurality of components, such as flaps 22, for blocking the entrance to the passage P. The flaps 22 may be partially attached to the balloon 12 (such as to necks 12*b*) or the shaft 16, such as by fixing at the proximal end of the flaps (corresponding to the proximal end of the balloon 12, including a connection to shaft 16), but unattached at the distal end (corresponding to the distal end of the balloon, such as including the tip). The situation could be reversed if the flaps 22 are positioned at the distal end of the balloon 12, or the flaps could be similarly arranged at the distal end.

Figure 7:
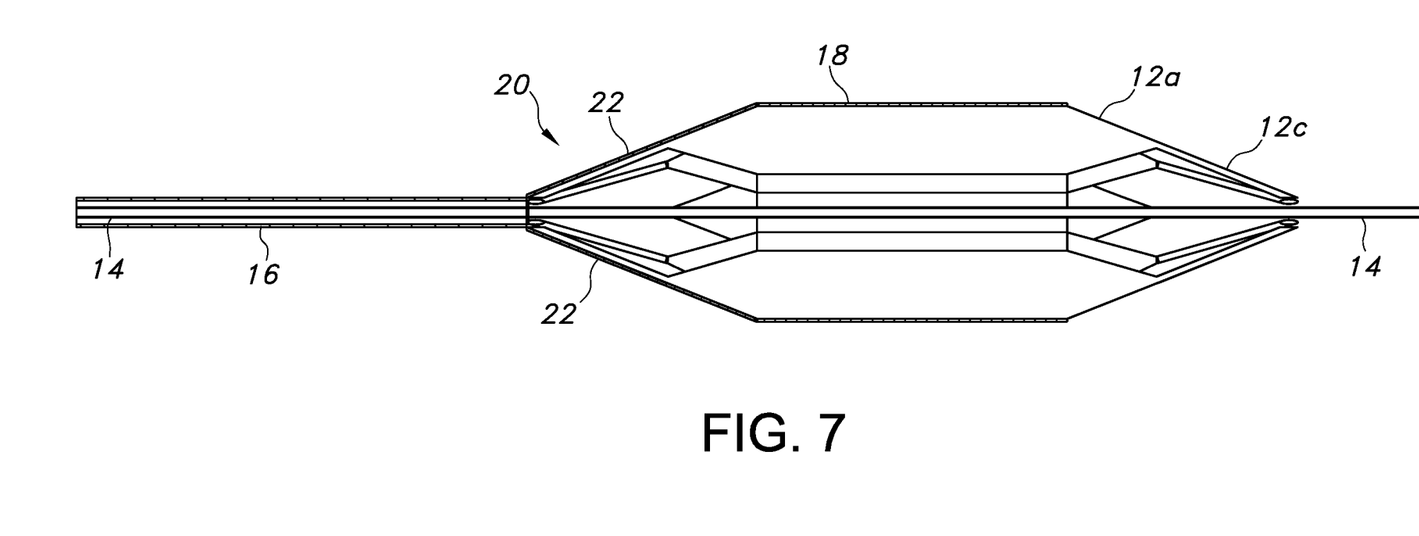
FIG. 7 is a cross-sectional view along line 7-7 of FIG. 6 with the valve in a first position for restricting flow through a central passage of the device.
Figure 8:
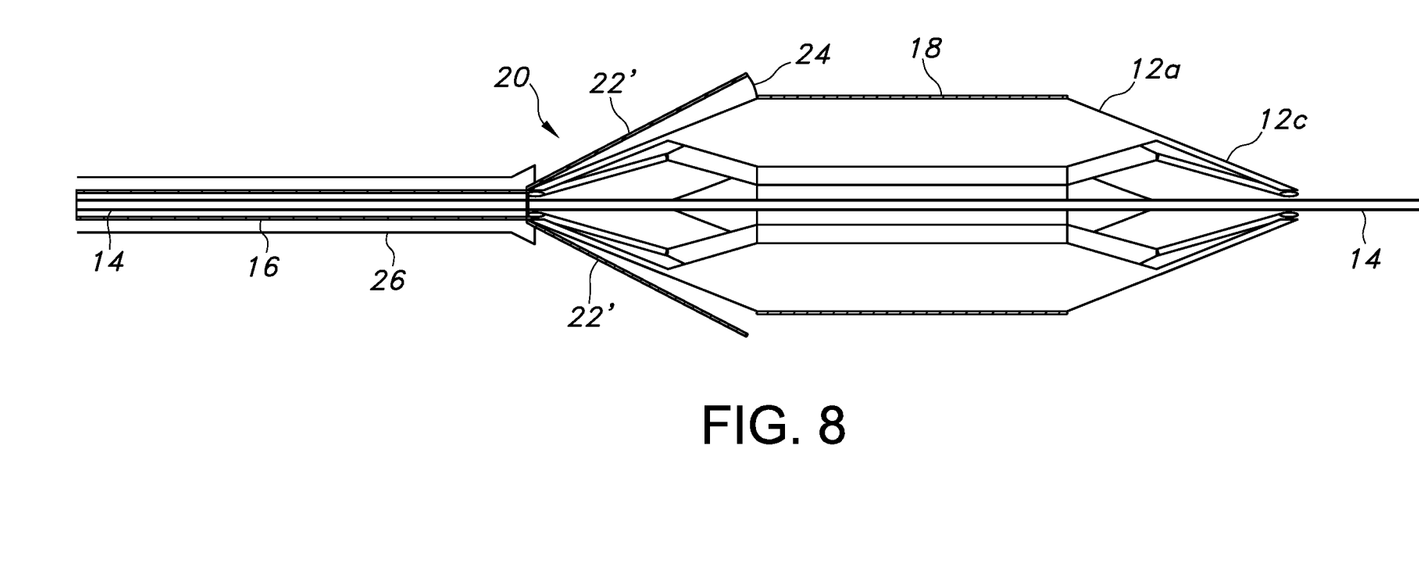
FIG. 8 is a cross-sectional side view of the device of FIG. 7, with the valve in a second position for permitting flow through a central passage of the device.

Consequently, as can be understood by comparing FIGS. 7 and 8, the flaps 22 may cover the entrance to the passage P in an unactuated condition, and then actuate (22' in FIG. 8) to allow fluid to flow through the passage, thereby creating a one way valve. One or more connectors, such as tether(s) 24, may also be provided to prevent one or more of the flaps 22 from folding or inverting. The tether 24 may be a thin, flexible structure, such as a wire, fiber, ribbon, or the like, so as to avoid significantly impeding the flow of fluid when the valve 20 is open (which could also be achieved by attaching the distal ends, such as to the necks 12*b* or another portion of the balloon 12).

Figure 6:
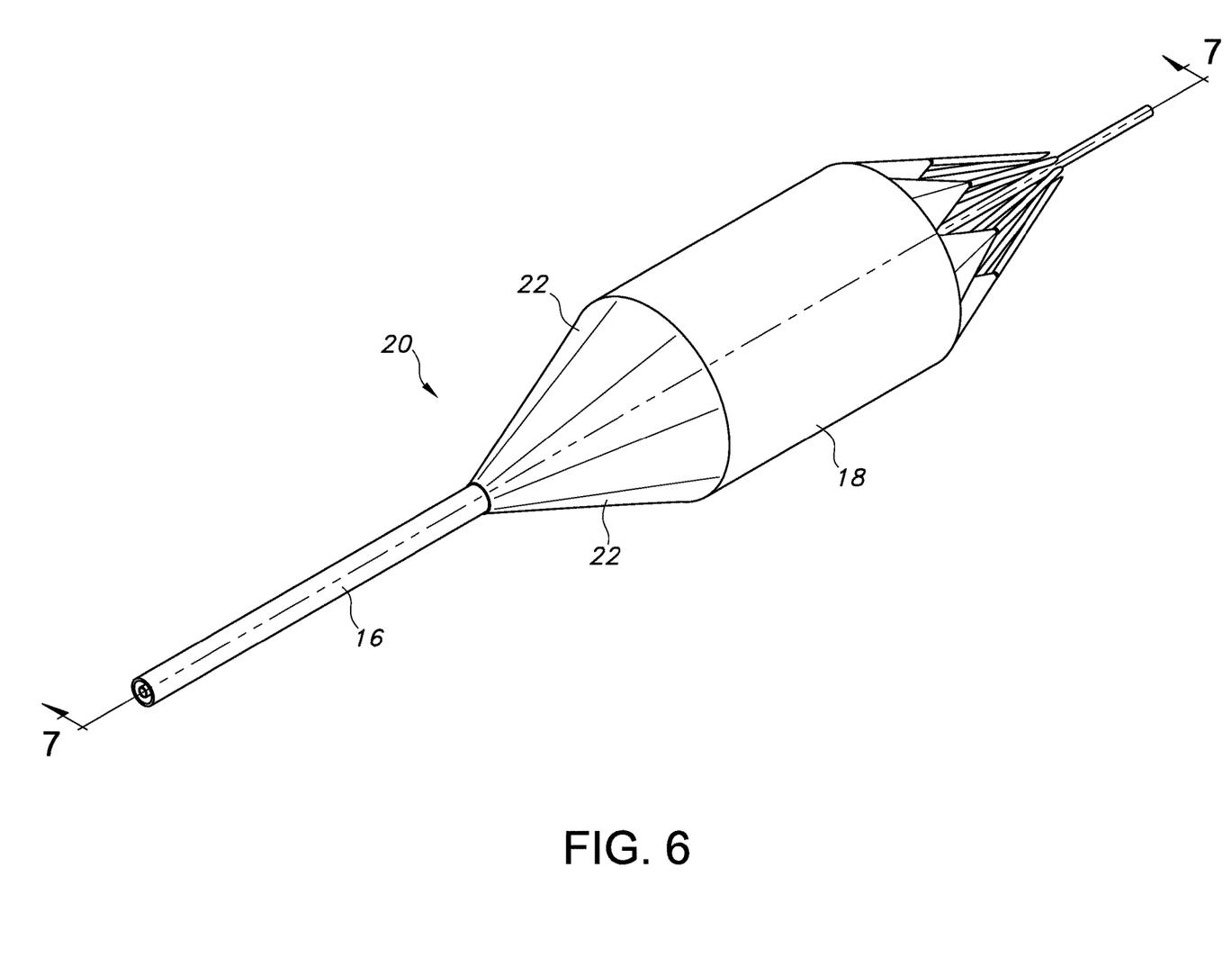
FIG. 6 is a perspective view of an inflatable device including a further embodiment of a valve.

An optional sheath 26 may also be provided to assist in the capture or retention of the flaps 22 for purposes of withdrawing the balloon 12 when deflated. Such a sheath 26 could also be used in connection with other of the disclosed embodiments, such as for example the extension 18*a* or the embodiments described below, including to withdraw the valve 20 and balloon 12, and/or to ensure that valving function is controlled or regulated.

Figure 9:
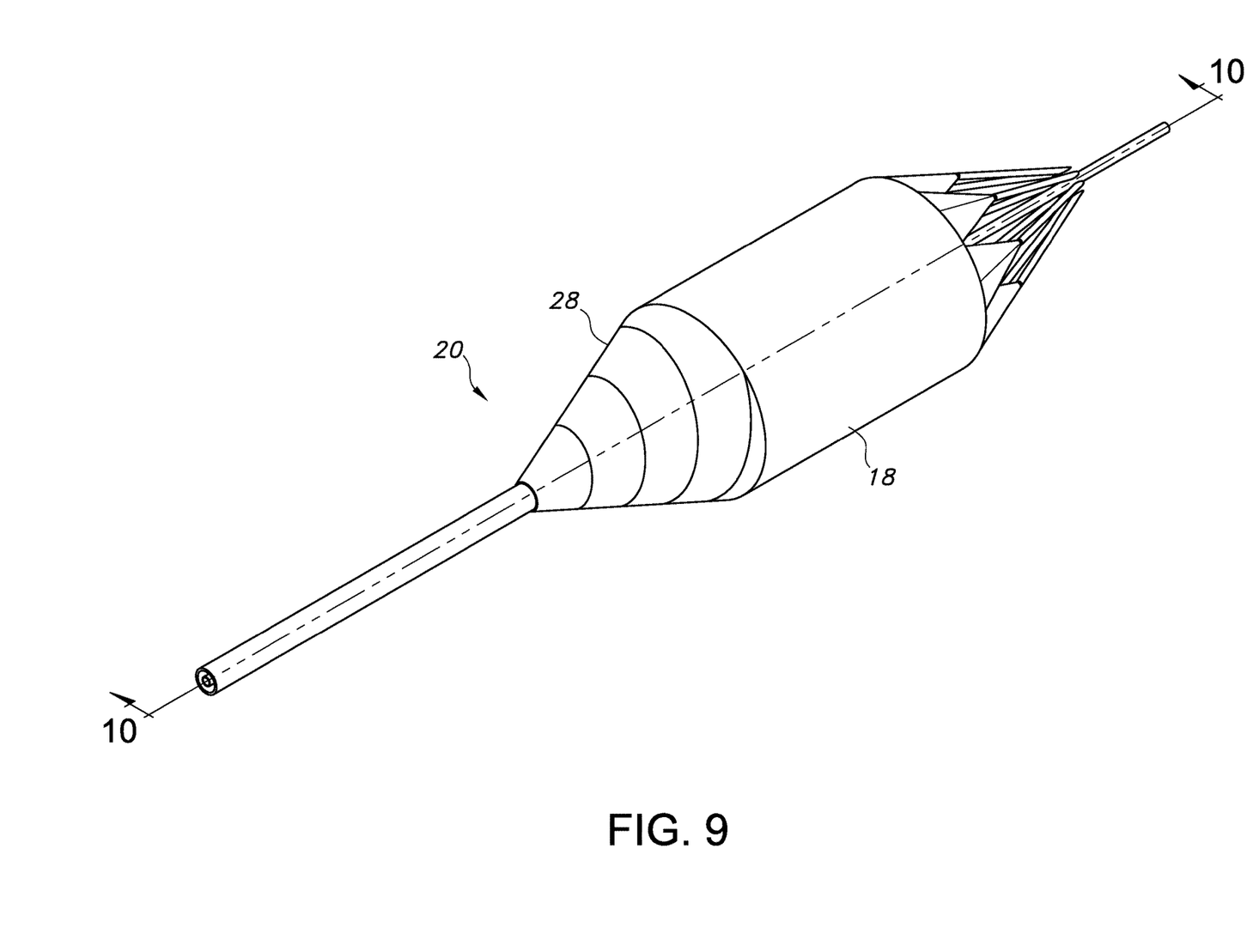
FIG. 9 is a perspective view of an inflatable device including a further embodiment of a valve.
Figure 10:
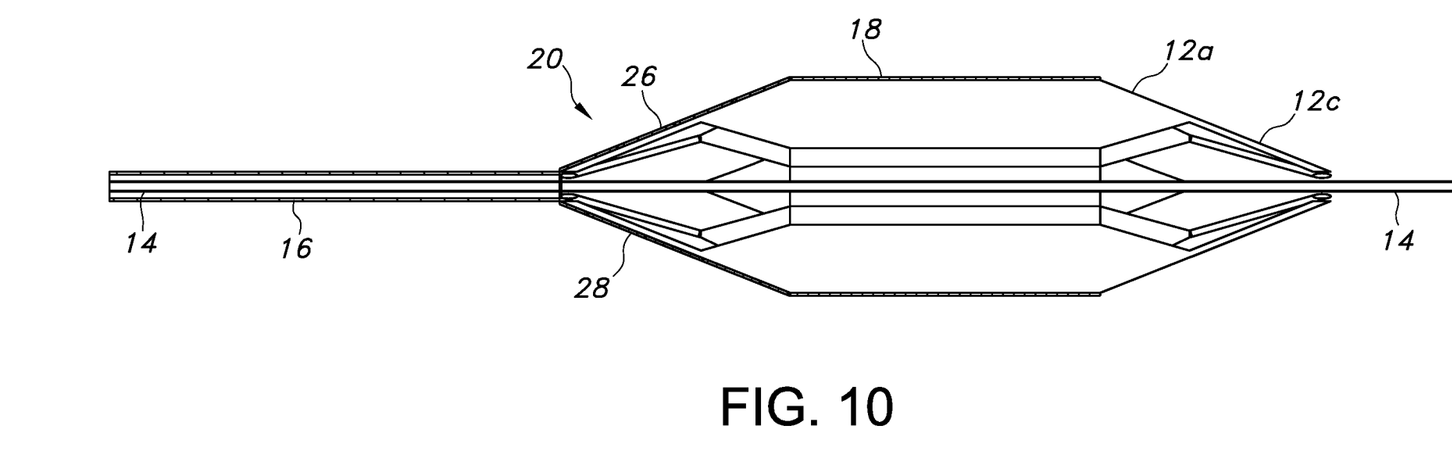
FIG. 10 is a cross-sectional view along line 10-10 of FIG. 9 with the valve in a first position for restricting flow through a central passage of the device.
Figure 11:
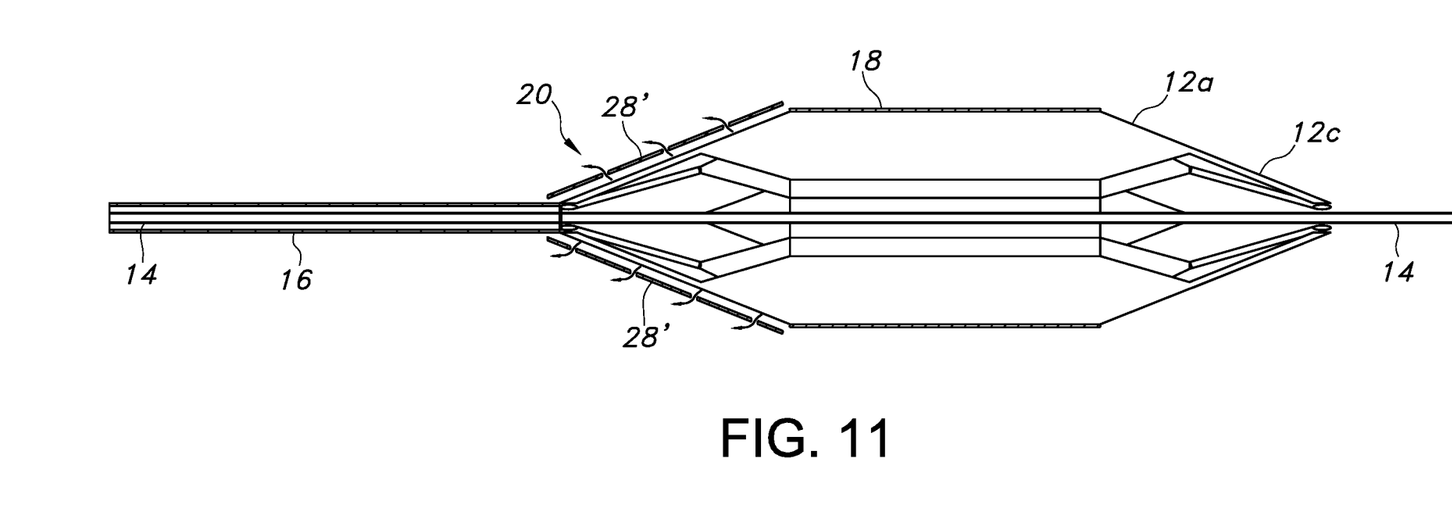
FIG. 11 is a cross-sectional side view of the device of FIG. 9, with the valve in a second position for permitting flow through a central passage of the device.

Another approach to an external valve 20 is illustrated with reference to FIGS. 9-11. In this arrangement, the valve 20 comprises a spiral covering 28. This covering 28 may either be an elongated piece of material wound spirally around the balloon 12, such as along and over the proximal necks 12*b*, of a piece of generally frusto-conical material that is spirally cut. The material forming the covering 28 may be connected at the proximal and distal end portions to the balloon 12 (either directly through bonding, or by way of a connector, such as a tether). The proximal end may alternatively be connected to the shaft 16. The material may also form an extension of the covering 18.

In any case, the gaps or cuts thus provided as a result of the spiral covering 28 allow for fluid flow from the passage P in the proximal direction in the illustrated embodiment (note 28' in FIG. 11), which may also result from movement of the material forming the spiral covering 28 in the axial or longitudinal direction. The resulting openings are then closed off when the fluid flow direction reverses to prevent flow in the opposite direction (including possibly by compression of the material forming the spiral covering in the longitudinal direction). A one way valve thus results. The aforementioned sheath (not shown) may also be used in this arrangement, as could the connectors or tethers.

Figure 12:
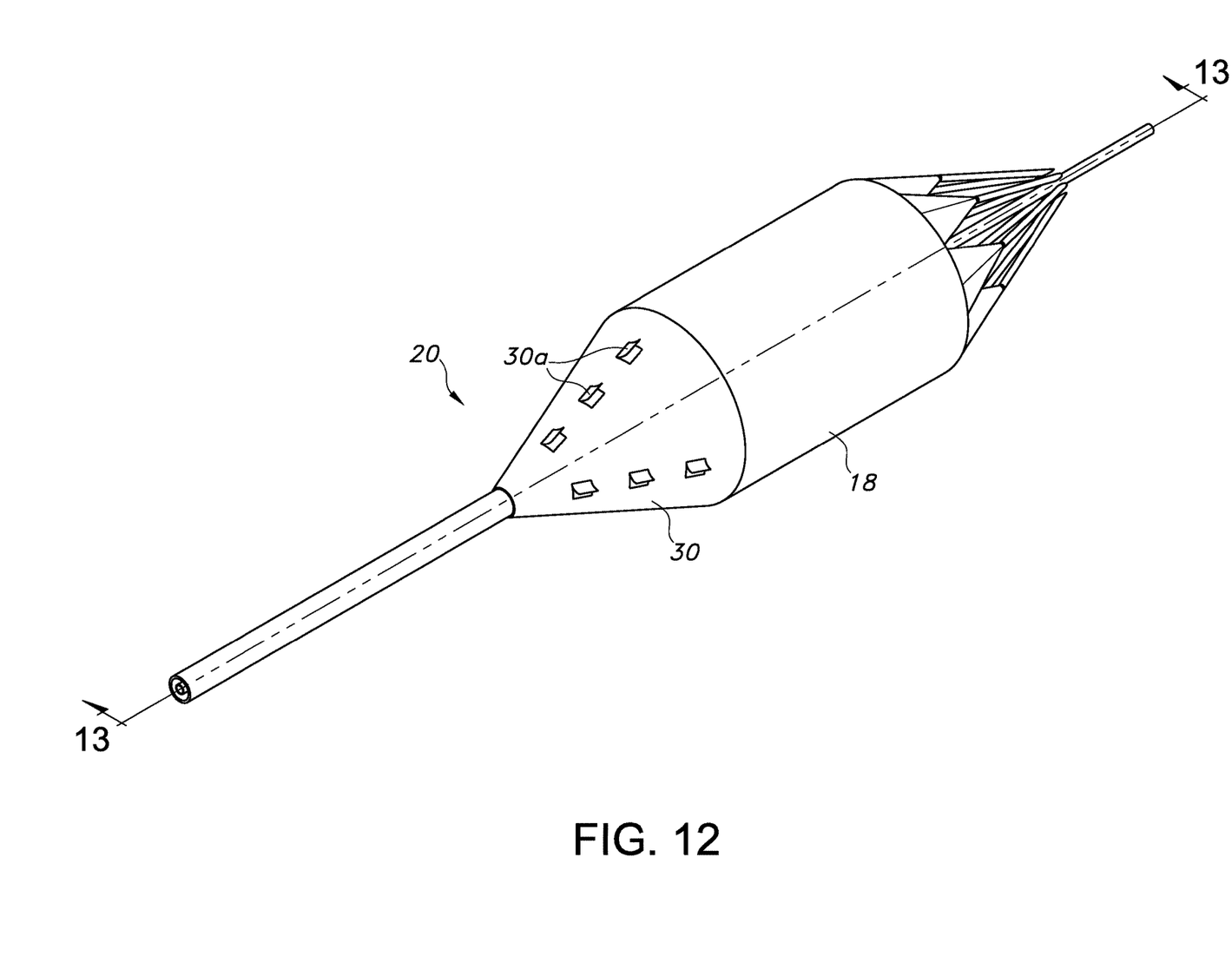
FIG. 12 is a perspective view of an inflatable device including a further embodiment of a valve.
Figure 13:
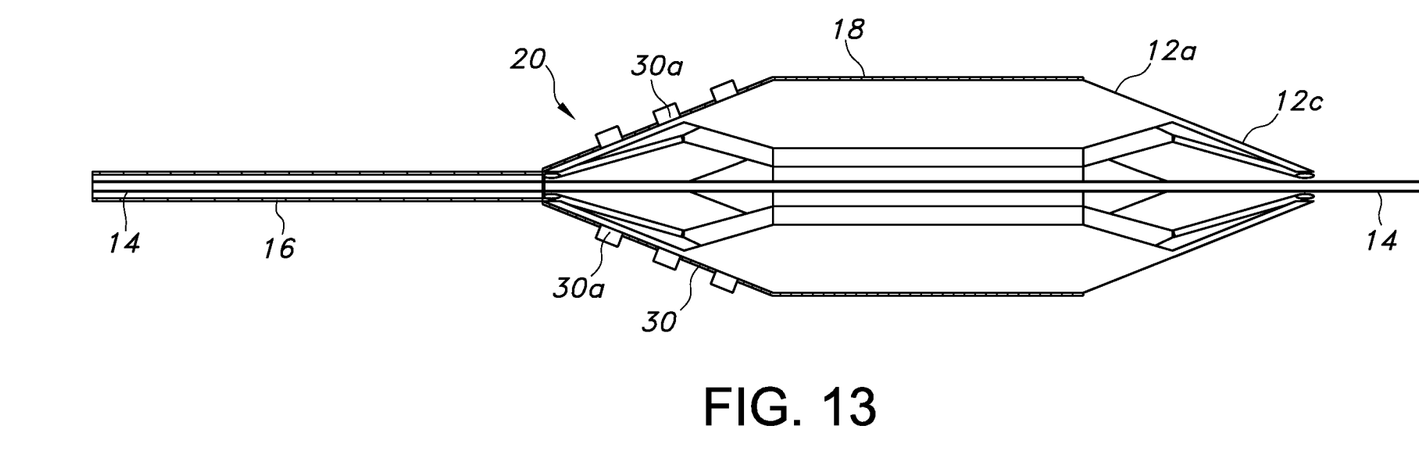
FIG. 13 is a cross-sectional view along line 13-13 of FIG. 12 with the valve in a first position for permitting flow through a central passage of the device.
Figure 14:
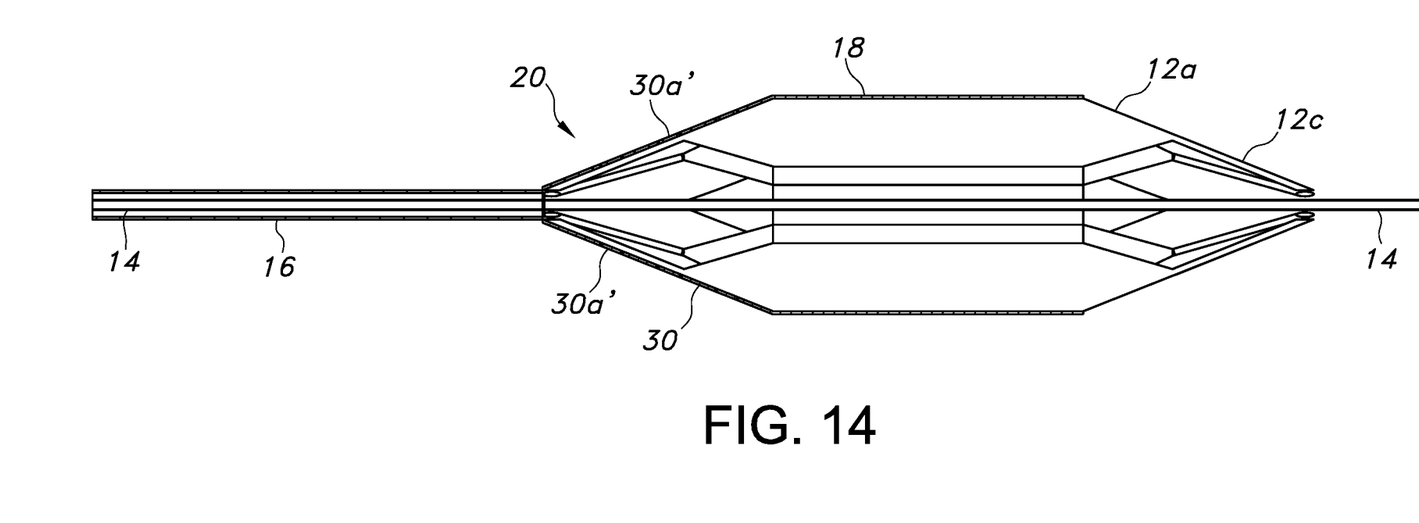
FIG. 14 is a cross-sectional side view of the device of FIG. 13, with the valve in a second position for restricting flow through a central passage of the device.

Still a further arrangement is illustrated in FIGS. 12-14. In this embodiment, a piece of frusto-conical material 30 is applied over the necks 12*b*, separate from the material forming the jacket or covering. This material 30 is provided with strategically positioned openings associated with movable parts of the material, such as flaps 30*a*. These flaps 30*a* may passively open (FIGS. 12 and 13) to allow fluid to flow to or from passage P, and then close (30*a*' in FIG. 14) to restrict the flow. While six flaps 30*a* are shown, it can be appreciated that any number may be provided along the entire circumference of the tapered portion of the balloon 12, as may be desired to achieve a particular degree of valving function. The flaps 18*a* may also be generally aligned in the longitudinal and circumferential directions, as shown, or may be irregularly spaced in either or both of these directions.

The flaps 30*a* may be formed by cutting the material 30, which may be a thin film (as contrasted with the jacket or covering 18, which is normally made of fibers and in a manner than renders the balloon 12 non-compliant when inflated), in a manner that simply leaves a hinge. Consequently, the flaps 30*a* are free to open and close in response to fluid flow, and thereby substantially obstruct the entrance and thus regulate the flow through passage P as a result. The opening and closing of the flaps 30*a* may be in any direction. The arrangement may also be provided in a manner that simulates fish gills, and thus the openings may simply be provided as slits that are not covered by separate flaps 30*a*, but simply open and close as a result of the flexing of the material.

Various materials may be used for forming the described structures, including as outlined in International Patent Application Publication No. WO2012099979A1.

The foregoing discussion is intended to provide an illustration of the inventive concepts, and is not intended to limit the invention to any particular mode or form. In all embodiments, the location or orientation of the valve 20 may be reversed (e.g., distal or proximal position, or alternate facing) for a transapical procedure. Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. Terms like "generally" or "substantially" mean that the value may vary depending on the circumstances, such as up to 10% of a given condition. The above-described configurations, elements or complete assemblies and methods and their elements for carrying out the invention, and variations of aspects of the invention can be combined and modified with each other in any combination, along with any obvious modifications.

The invention claimed is:

1. An apparatus for performing a medical procedure in a vessel for transmitting a flow of fluid, comprising:
   an inflatable perfusion balloon including an internal passage for permitting the fluid flow in the vessel while the perfusion balloon is in an inflated condition; and
   a valve associated with the balloon for controlling the fluid flow within the passage, the valve comprising a plurality of elongated flaps, each of the plurality of flaps for selectively covering an entrance to the passage to control the flow of fluid therein, wherein each flap includes a fixed proximal end;
   at least one tether for tethering at least one of the flaps to the balloon, wherein at least one flap of the plurality of flaps includes a distal end connected to the balloon by the tether.

2. The apparatus of claim 1, wherein the balloon comprises a generally tapered portion, and the flaps extend along the generally tapered portion.

3. The apparatus of claim 1, wherein the at least one tethers comprises a plurality of tethers, one tether for tethering each of the flaps to the balloon.

4. The apparatus of claim 1, wherein the flaps are narrower at the fixed proximal end than at a distal end.

5. The apparatus of claim 1, further including a sheath for covering the plurality of flaps.

6. An apparatus for performing a medical procedure in a vessel for transmitting a flow of fluid, comprising:
   a shaft;
   an inflatable perfusion balloon including an internal passage formed between an inner surface of the inflatable perfusion balloon and the shaft for permitting the fluid flow in the vessel while the perfusion balloon is in an inflated condition; and
   a valve associated with the balloon for controlling the fluid flow within the passage, the valve comprising a plurality of elongated flaps, each of the plurality of flaps for selectively covering an entrance to the internal passage to control the flow of fluid therein, wherein each flap includes a fixed proximal end;
   at least one tether for tethering at least one of the flaps to the balloon, wherein at least one flap of the plurality of flaps includes a distal end connected to the balloon by the tether.

7. The apparatus of claim 6, wherein the at least one tethers comprises a plurality of tethers, one tether for tethering each of the flaps to the balloon.

8. An apparatus for performing a medical procedure in a vessel for transmitting a flow of fluid, comprising:
   a shaft;
   an inflatable perfusion balloon comprising a plurality of inflatable cells in a single cross-section, the plurality of inflatable cells bounding an internal passage formed between the inflatable perfusion balloon and the shaft for permitting the fluid flow in the vessel while the perfusion balloon is in an inflated condition; and
   a valve associated with the balloon for controlling the fluid flow within the passage, the valve comprising a plurality of elongated flaps, each of the plurality of flaps for selectively covering an entrance to the internal passage to control the flow of fluid therein, wherein each flap includes a fixed proximal end;
   at least one tether for tethering at least one of the flaps to the balloon, wherein at least one flap of the plurality of flaps includes a distal end connected to the balloon by the tether.

9. The apparatus of claim 8, wherein the at least one tethers comprises a plurality of tethers, one tether for tethering each of the flaps to the balloon.

\* \* \* \* \*